United States Patent
Kanasaki et al.

(10) Patent No.: US 6,399,567 B1
(45) Date of Patent: Jun. 4, 2002

(54) CYCLIC HEXAPEPTIDES HAVING ANTIBIOTIC ACTIVITY

(75) Inventors: Ryuichi Kanasaki, Toride; Shigehiro Takase, Ishioka; Michizane Hashimoto, Tsuchiura; Hiroshi Hatanaka, Ibaraki; Kazutoshi Sakamoto, Tsuchiura; Seiji Hashimoto, Tsukuba; Nobuyuki Shiraishi, Ikeda; Hidenori Ohki, Takarazuka; Kohji Kawabata, Kawanishi, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/308,218
(22) PCT Filed: Nov. 18, 1997
(86) PCT No.: PCT/JP97/04194
§ 371 (c)(1),
(2), (4) Date: Jun. 16, 1999
(87) PCT Pub. No.: WO98/22498
PCT Pub. Date: May 28, 1998

(30) Foreign Application Priority Data

Nov. 19, 1996 (AU) .................................................. PO3715

(51) Int. Cl.$^7$ ............................... A61K 38/12; A61K 38/08
(52) U.S. Cl. ............................ 514/11; 514/9; 530/317; 530/323
(58) Field of Search ...................... 514/9, 11; 530/317

(56) References Cited

U.S. PATENT DOCUMENTS 5,502,033 A * 3/1996 Iwamoto et al. ............... 514/11

FOREIGN PATENT DOCUMENTS

WO        96/11210    * 4/1996

* cited by examiner

Primary Examiner—Michael Borin
(74) Attorney, Agent, or Firm—Oblon, Spivak, McClelland, Maier & Neustadt, P.C.

(57) ABSTRACT

This invention relates to new polypeptide compounds represented by the following formula (I):

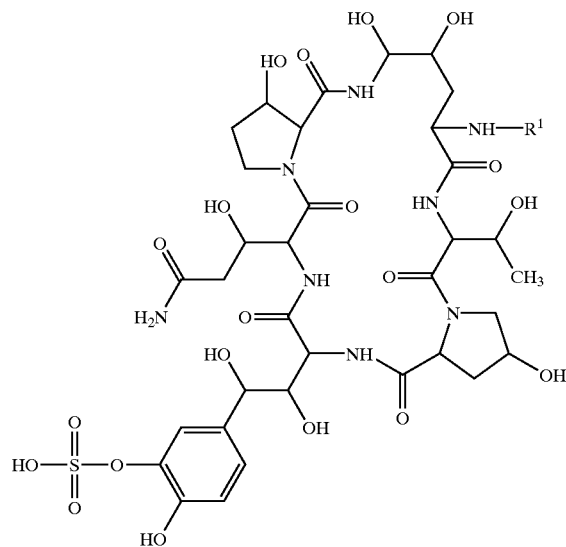

wherein $R^1$ is as defined in the description or a salt thereof which have antimicrobial activities (especially, antifungal activities), inhibitory activity on β-1,3-glucan synthase, to process for preparation thereof, to a pharmaceutical composition comprising the same, and to a method for the prophylactic and/or therapeutic treatment of infectious disease including *Pneumocystis carinii* infection (e.g., *Pneumocystis carinii* pneumonia) in a human being or an animal.

7 Claims, No Drawings

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial  Sequence:peptide
<221> NAME/KEY: MOD_RES
<222> LOCATION: (1)
<223> OTHER INFORMATION: 4Hyp
<221> NAME/KEY: MOD_RES
<222> LOCATION: (2)
<223> OTHER INFORMATION: substituted wit hydroxyl and substituted phenyl
<221> NAME/KEY: MOD_RES
<222> LOCATION: (3)
<223> OTHER INFORMATION: substituted with hydroxyl
<221> NAME/KEY: MOD_RES
<222> LOCATION: (4)
<223> OTHER INFORMATION: 3Hyp
<221> NAME/KEY: MOD_RES
<222> LOCATION: (5)
<223> OTHER INFORMATION: Orn, substituted with hydroxyl, acylated
<223> OTHER INFORMATION: The 5 amino group o f Ornithine at position 5 is
      linked to the carboxyl group of Proline at
      position 4 by a peptide  link age
<223> OTHER INFORMATION: Threonine at position 6 is linked to Proline at
      position 1 by a peptide linkage

<400> SEQUENCE: 1

Pro Thr Gln Pro Xaa Thr
 1               5
```

CYCLIC HEXAPEPTIDES HAVING ANTIBIOTIC ACTIVITY

TECHNICAL FIELD

The present invention relates to new polypeptide compound and a pharmaceutically acceptable salt thereof which are useful as a medicament.

BACKGROUND ART

In U.S. Pat. No. 5,376,634, U.S. Pat. No. 5,502,033, etc., there are disclosed the polypeptide compound and a pharmaceutically acceptable salt thereof, which have antimicrobial activities (especially antifungal activity).

DISCLOSURE OF INVENTION

The present invention relates to new polypeptide compound and a pharmaceutically acceptable salt thereof.

More particularly, it relates to new polypeptide compound and a pharmaceutically acceptable salt thereof, which have antimicrobial activities [especially, antifungal activities, in which the fungi may include Asperaillus, Cryptococcus, Candida, Mucor, Actinomyces, Histoplasma, Dermatophyte, Malassezia, Fusarium and the like.], inhibitory activity on β-1,3-glucan synthase, and further which are expected to be useful for the prophylactic and/or therapeutic treatment of *Pneumocystis carinii* infection (e.g. *Pneumocystis carinii* pneumonia) in a human being or an animal, and further the toxicity of which are expected to be much lower in comparison with the former polypeptide compounds, to a process for preparation thereof, to a pharmaceutical composition comprising the same, and to a method for the prophylactic and/or therapeutic treatment of infectious diseases including *Pneumocystis carinii* infection (e.g. *Pneumocystis carinii* pneumonia) in a human being or an animal.

The object polypeptide compound of the present invention is new and can be represented by the following general formula [I]: (SEQ ID NO: 1)

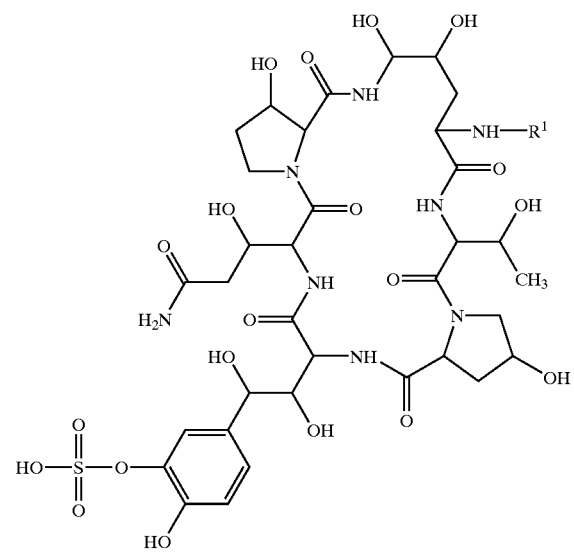

wherein $R^1$ is hydrogen or acyl group, or a salt thereof.

The polypeptide compound [I] of the present invention can be prepared by the processes as illustrated in the following schemes.

Process 1 a strain belonging to the Coleophoma which is capable of producing the compound [Ia] or a salt thereof   fermentation→

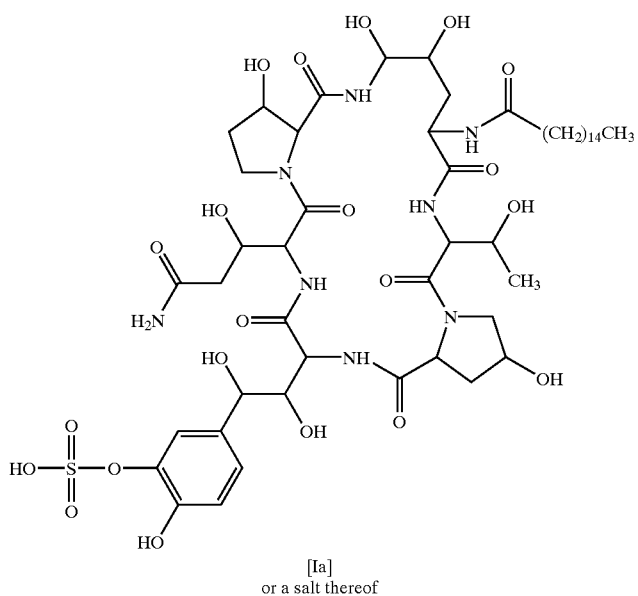

[Ia] or a salt thereof

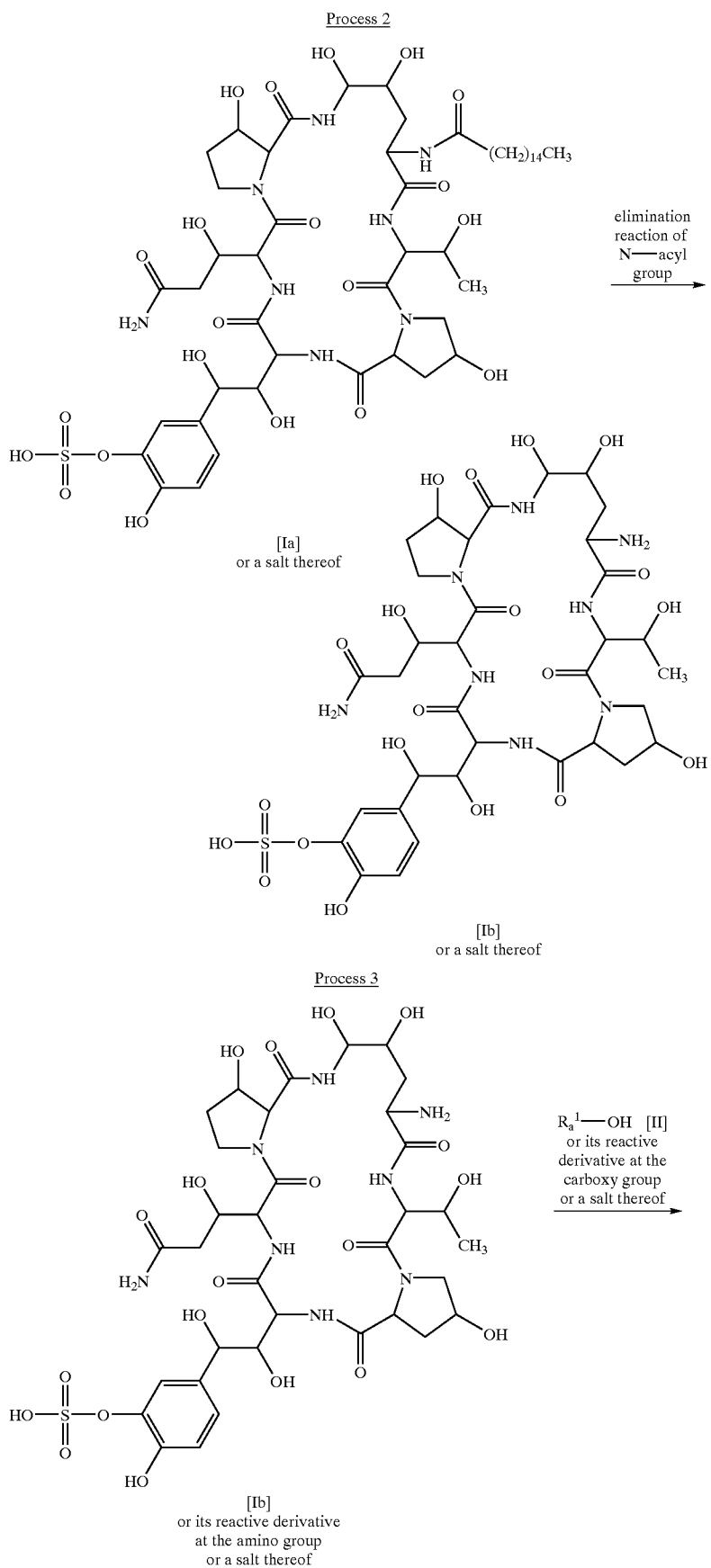

-continued

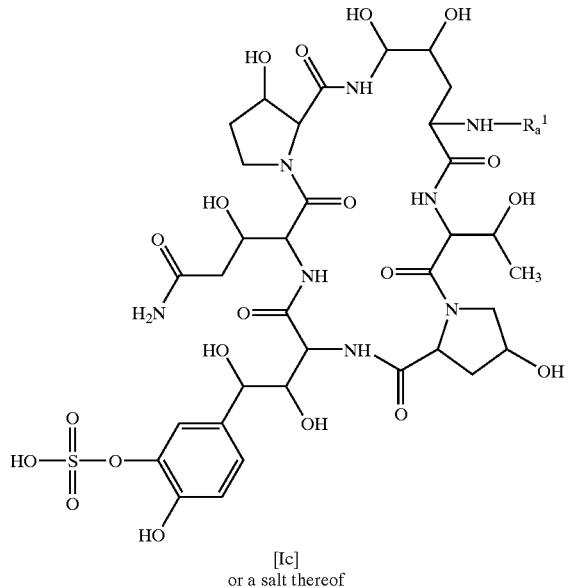

[Ic]
or a salt thereof wherein $R_a^1$ is acyl group.

Suitable salt of the object compound [I] is a pharmaceutically acceptable salt such as conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent description of this specification, suitable examples of the various definitions are explained in detail as follows:

The term "lower" is intended to mean 1 to 6 carbon atom(s), unless otherwise indicated.

The term "higher" is intended to mean 7 to 20 carbon atoms, unless otherwise indicated.

Suitable "acyl group" may be aliphatic acyl, aromatic acyl, heterocyclic acyl, arylaliphatic acyl and heterocyclicaliphatic acyl derived from carboxylic acid, carbonic acid, carbamic acid, sulfonic acid, and the like.

Suitable example of the "acyl group" thus explained may be:

lower alkanoyl [e.g. formyl, acetyl, propionyl, butyryl, isobutyryl, valeryl, hexanoyl, pivaloyl, etc.] which may have one or more (preferably 1 to 3) suitable substituent(s) such as halogen (e.g. fluoro, chloro, bromo, iodo); aryl (e.g. phenyl, naphthyl, anthryl, etc.) which may have one or more (preferably 1 to 3) suitable substituent(s) like hydroxy, higher alkoxy as explained below, aforesaid aryl, or the like; lower alkoxy as explained below; amino; protected amino, preferably, acylamino such as lower alkoxycarbonylamino (e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc.); or the like; di(lower)alkylamino (e.g. dimethylamino, N-methylethylamino, diethylamino, N-propylbutylamino, dipentylamino, dihexylamino, etc.); lower alkoxyimino (e.g. methoxyimino, ethoxyimino, propoxyimino, butoxyimino, t-butoxyimino, pentyloxyimino, hexyloxyimino, etc.); ar(lower)alkoxyimino such as phenyl(lower)alkoxyimino (e.g. benzyloxyimino, phenethyloxyimino, benzhydryloxyimino, etc.) which may have one or more (preferably 1 to 3) suitable substituent(s) like higher alkoxy as explained below, or the like; heterocyclicthio, preferably, pyridylthio, which may have one or more (preferably 1 to 3) suitable substituent(s) like higher alkyl (e.g. heptyl, octyl, 2-ethylhexyl, nonyl, decyl, 3,7-dimethyloctyl, undecyl, dodecyl, tridecyl, tetradecyl, pentadecyl, 3-methyl-10-ethyldodecyl, hexadecyl, heptadecyl, octadecyl, nonadecyl, icosyl, etc.), or the like; heterocyclic group (e.g. thienyl, imidazolyl, pyrazolyl, furyl, tetrazolyl, thiazolyl, thiadiazolyl, etc.) which may have one or more (preferably 1 to 3) suitable substituent(s) like amino, aforesaid protected amino, aforesaid higher alkyl, or the like; or the like;

higher alkanoyl [e.g. heptanoyl, octanoyl, nonanoyl, decanoyl, undecanoyl, lauroyl, tridecanoyl, myristory, pentadecanoyl, palmitoyl, 10,12-dimethyltetradecanoyl, heptadecanoyl, stearoyl, nonadecanoyl, icosanoyl, etc.], in which the preferred one may be $(C_7-C_{17})$alkanoyl, and the most preferred one may be palmitoyl;

lower alkenoyl [e.g. acryloyl, methacryloyl, crotonoyl, 3-pentenoyl, 5-hexenoyl, etc.] which may have one or more (preferably 1 to 3) suitable substituent(s) such as aforesaid aryl which may have one or more (preferably 1 to 3) suitable substituent(s) like higher alkoxy as explained below, or the like, or the like;

higher alkenoyl [e.g. 4-heptenoyl, 3-octenoyl, 3,6-decadienoyl, 3,7,11-trimethyl-2,6,10-dodecatrienoyl, 4,10-heptadecadienoyl, etc.];

lower alkoxycarbonyl [e.g. methoxycarbonyl, ethoxycarbonyl, propoxycarbonyl, butoxycarbonyl, t-butoxycarbonyl, pentyloxycarbonyl, hexyloxycarbonyl, etc.];

higher alkoxycarbonyl [e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, icosyloxycarbonyl, etc.];

aryloxycarbonyl [e.g. phenoxycarbonyl, naphthyloxycarbonyl, etc.];

arylglyoxyloyl [e.g. phenylglyoxyloyl, naphthylglyoxyloyl, etc.];

ar(lower)alkoxycarbonyl which may have one or more suitable substituent(s) such as phenyl(lower)alkoxycarbonyl which may have nitro or lower alkoxy [e.g. benzyloxycarbonyl, phenethyloxycarbonyl, p-nitrobenzyloxycarbonyl, p-methylbenzyloxycarbonyl, etc.];

lower alkylsulfonyl [e.g. methylsulfonyl, ethylsulfonyl, propylsulfonyl, isopropylsulfonyl, pentylsulfonyl, butylsulfonyl, etc.];

arylsulfonyl [e.g. phenylsulfonyl, naphthylsulfonyl, etc.] which may have one or more (preferably 1 to 3) suitable substituent(s) such as lower alkyl as explained below, higher alkoxy as explained below, or the like;

ar(lower)alkylsulfonyl such as phenyl(lower)alkylsulfonyl [e.g. benzylsulfonyl, phenethylsulfonyl, benzhydrylsulfonyl, etc.], or the like;

aroyl [e.g. benzoyl, naphthoyl, anthrylcarbonyl, etc.] which may have one or more (preferably 1 to 5) suitable substituent(s) such as aforesaid halogen; lower alkyl (e.g. methyl, ethyl, propyl, butyl, t-butyl, pentyl, hexyl, etc.); aforesaid higher alkyl; lower alkoxy (e.g. methoxy, ethoxy, propoxy, butoxy, t-butoxy, pentyloxy, hexyloxy, etc.) which may have one or more (preferably 1 to 10) suitable substituent(s) like aforesaid lower alkoxy, aforesaid halogen, aforesaid aryl, or the like; higher alkoxy (e.g. heptyloxy, octyloxy, 2-ethylhexyloxy, nonyloxy, decyloxy, 3,7-dimethyloctyloxy, undecyloxy, dodecyloxy, tridecyloxy, tetradecyloxy, pentadecyloxy, 3-methyl-10-ethyldodecyloxy, hexadecyloxy, heptadecyloxy, octadecyloxy, nonadecyloxy, icosyloxy, etc.) which may have one or more (preferably 1 to 17) suitable substituent(s) like aforesaid halogen, in which the preferred one may be aroyl having ($C_7$–$C_{17}$)alkoxy, and the more preferred one may be benzoyl having ($C_7$–$C_{17}$)alkoxy, and the most preferred one may be benzoyl having octyloxy; higher alkenyloxy (e.g. 3-heptenyloxy, 7-octenyloxy, 2,6-octadienyloxy, 5-nonenyloxy, 1-decenyloxy, 3,7-dimethyl-6-octenyloxy, 3,7-dimethyl-2,6-octadienyloxy, 8-undecenyloxy, 3,6,8-dodecatrienyloxy, 5-tridecenyloxy, 7-tetradecenyloxy, 1,8-pentadecadienyloxy, 15-hexadecenyloxy, 11-heptadecenyloxy, 7-octadecenyloxy, 10-nonadecenyloxy, 18-icosenyloxy, etc.); carboxy;

aforesaid aryl which may have one or more (preferably 1 to 3) suitable substituent(s) like aforesaid higher alkoxy; aryloxy (e.g. phenoxy, naphthyloxy, anthryloxy, etc.) which may have one or more (preferably 1 to 3) suitable substituent(s) like aforesaid lower alkoxy, or aforesaid higher alkoxy; aroyl substituted with heterocyclic group which has aryl having lower alkoxy; aroyl substituted with heterocyclic group which has aryl having higher alkoxy;

ar(lower)alkenoyl substituted with aryl having lower alkoxy; ar(lower)alkenoyl substituted with aryl having higher alkoxy; aroyl substituted with aryl which has aryl having lower alkoxy; aroyl substituted with aryl which has aryl having higher alkoxy; and the like.

Suitable example of "aroyl" may include benzoyl, toluoyl, naphthoyl, anthrylcarbonyl, and the like, in which the preferred one may be benzoyl.

Suitable example of "aryl" and "ar" moiety may include phenyl which may have lower alkyl (e.g., phenyl, mesityl, tolyl, etc.), naphthyl, anthryl, and the like, in which the preferred one may be phenyl.

Suitable example of "lower alkoxy" may include straight or branched one such as methoxy, ethoxy, propoxy, isopropoxy, butoxy, isobutoxy, tert-butoxy, pentyloxy, tert-pentyloxy, neo-pentyloxy, hexyloxy, isohexyloxy, and the like.

Suitable example of "higher alkoxy" may include straight or branched one such as heptyloxy, octyloxy, 3,5-dimethyloctyloxy, 3,7-dimethyloctyloxy, nonyloxy, decyloxy, undecyloxy, dodecyloxy, tridecyloxy, tetradecyloxy, hexadecyloxy, heptadecyloxy, octadecyloxy, nonadecyloxy, icosyloxy, and the like, in which the preferred one may be ($C_7$–$C_{17}$)alkoxy.

Suitable example of "heterocyclic group" and "heterocyclic" moiety may include unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, syndonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl, (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

saturated 3 to 8-membered (more preferably 5 or 6-membered) heteromonocyclic group containing an oxygen atom, for example, tetrahydrofuran, tetrahydropyran, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like, in which the preferred one may be saturated 3 to 8-membered heteromonocyclic group containing 1 to 4 nitrogen atom(s) and unsaturated 3 to 8-membered heteromonocyclic group containing 1 to 2 oxygen atom(s) and 1 to 3 nitrogen atom(s).

Suitable example of "aroyl substituted with heterocyclic group which has aryl having lower alkoxy" may be benzoyl substituted with saturated 6-membered heteromonocyclic group containing 1 to 4 nitrogen atom(s) which has phenyl having ($C_4$–$C_6$)alkoxy, benzoyl substituted with unsaturated 5-membered heteromonocyclic group containing 1 to 2 sulfur atom(s) and 1 to 3 nitrogen atom(s) which has phenyl having ($C_4$–$C_6$) alkoxy or benzoyl substituted with unsaturated 5-membered heteromonocyclic group containing 1 to 2 oxygen atom(s) and 1 to 3 nitrogen atom(s) which has phenyl having ($C_4$–$C_6$)alkoxy, in which the preferred one may be benzoyl substituted with piperazinyl which has phenyl having ($C_4$–$C_6$)alkoxy, benzoyl substituted with thiadiazolyl which has phenyl having ($C_4$–$C_6$)alkoxy or benzoyl substituted with isoxazolyl which has phenyl having ($C_4$–$C_6$)alkoxy, and the most preferred one may be benzoyl substituted with piperazinyl which has phenyl having hexyloxy, benzoyl substituted with thiadiazolyl which has phenyl having hexyloxy or benzoyl substituted with isoxazolyl which has phenyl having pentyloxy.

Suitable example of "ar(lower)alkenoyl substituted with aryl having lower alkoxy" may be phenyl($C_3$–$C_6$)alkenoyl substituted with phenyl having ($C_4$–$C_6$)alkoxy, in which the preferred one may be phenylacryloyl substituted with phenyl having pentyloxy.

Suitable example of "aroyl substituted with aryl which has aryl having lower alkoxy" may be benzoyl substituted with phenyl which has phenyl having ($C_4$–$C_6$)alkoxy, in which the preferred one may be benzoyl substituted with phenyl which has phenyl having pentyloxy.

The process for preparing the object compound [I] or a salt thereof of the present invention is explained in detail in the following.

Process 1

The object polypeptide compound [Ia] or a salt thereof can be prepared by the fermentation process.

The fermentation process is explained in detail in the following.

The compound [Ia] or a salt thereof of this invention can be produced by fermentation of the compound [Ia] or a salt thereof-producing strain belonging to the genus Coleophoma such as Coleophoma sp. F-11899 in a nutrient medium in the presence of leucine.

(i) Microorganism

Particulars of the microorganism used for producing the compound [Ia] or a salt thereof is explained in the following.

The strain F-11899 was originally isolated from a soil sample collected at Iwaki-shi, Fukushima-ken, Japan. This organism grew rather restrictedly on various culture media, and formed dark grey to brownish grey colonies. Anamorph (conidiomata) produced on a steam-sterilized leaf segment affixed on a Miura's LCA plate[1]) or a corn meal agar plate by inoculating the isolate, while neither teleomorph nor anamorph formed on the agar media. Its morphological, cultural and physiological characteristics are as follows.

Cultural characteristics on various agar media are summarized in Table 1. Cultures on potato dextrose agar grew rather rapidly, attaining 3.5–4.0 cm in diameter after two weeks at 25° C. This colony surface was plane, felty, somewhat wrinkly and brownish grey. The colony center was pale grey to brownish grey, and covered with aerial hyphae. The reverse color was dark grey. Colonies on malt extract agar grew more restrictedly, attaining 2.5–3.0 cm in diameter under the same conditions. The surface was plane, thin to felty and olive brown. The colony center was yellowish grey, and covered with aerial hyphae. The reverse was brownish grey.

The morphological characteristics were determined on basis of the cultures on a sterilized leaf affixed to a Miura's LCA plate. Conidiomata formed on the leaf segment alone. They were pycnidial, superficial, separate, discoid to ampulliform, flattened at the base, unilocular, thin-walled, black, 90–160(–200) μm in diameter and 40–70 μm high. Ostiole was often single, circular, central, papillate, 10–30 μm in diameter and 10–20 μm high. Conidiophores formed from the lower layer of inner pycnidial walls. They were hyaline, simple or sparingly branched, septate and smooth. Conidiogenous cells were enteroblastic, phialidic, determinate, ampulliform to obpyriform, hyaline, smooth, 5–8×4–6 μm, with a collarette. The collarettes were campanulate to cylindrical, and 14–18×3–5 μm. Conidia were hyaline, cylindrical, thin-walled, aseptate, smooth and 14–16(–18)×2–3 μm.

The vegetative hyphae were septate, brown, smooth and branched. The hyphal cells were cylindrical and 2–7 μm thick. The chlamydospores were absent.

The strain F-11899 had a temperature range for growth of 0 to 31° C. and an optimum temperature of 23 to 27° C. on potato dextrose agar.

The above characteristics indicate that the strain F-11899 belongs to the order Coelomycetes[2, 3, 4]. Thus, we named the strain "Coelomycetes strain F-11899".

TABLE 1

Cultural characteristics of the strain F-11899

| Medium | Cultural characteristics |
|---|---|
| Malt extract agar (Blakeslee 1915) | G: Rather restrictedly, 2.5–3.0 cm<br>S: Circular, plane, thin to felty, olive brown (4F5), arising aerial hyphae at the center (yellowish grey (4B2)<br>R: Brownish grey (4F2) |

TABLE 1-continued

Cultural characteristics of the strain F-11899

| Medium | Cultural characteristics |
|---|---|
| Potato dextrose agar (Difco 0013) | G: Rather rapidly, 3.5–4.0 cm<br>S: Circular, plane, felty, somewhat wrinkly, brownish grey (4F2), arising aerial hyphae at the center (pale grey (4B1) to brownish grey (4F2))<br>R: Dark grey (4F1) |
| Czapeck's solution agar (Raper and Thom 1949) | G: Very restrictedly, 1.0–1.5 cm<br>S: Irregular, thin, scanty, immersed, subhyaline to white<br>R: Subhyaline to white |
| Sabouraud dextrose agar (Difco 0109) | G: Restrictedly, 2.0–2.5 cm<br>S: Circular, plane, thin, white, sectoring, light brown (6D5) at the colony center<br>R: Pale yellow (4A3) |
| Oatmeal agar (Difco 0552) | G: Fairly rapidly, 4.0–4.5 cm<br>S: Circular, plane, felty to cottony, dark grey (4F1) to brownish grey (4F2)<br>R: Brownish grey (4D2) |
| Emerson Yp Ss agar (Difco 0739) | G: Restrictedly, 2.0–2.5 cm<br>S: Circular to irregular, plane, felty, dark grey (4F1) to brownish grey (4F2)<br>R: Medium grey (4E1) to dark grey (4F1) |
| Corn meal agar (Difco 0386) | G: Rather restrictedly, 2.5–3.0 cm<br>S: Circular, plane, thin to felty, dark grey (2F1) to olive (2F3)<br>R: Dark grey (2F1) to olive (2F3) |
| MY20 agar | G: Restrictedly, 1.5–2.0 cm<br>S: Circular to irregular, thin, sectoring, yellowish white (4A2)<br>R: Pale yellow (4A3) to orange white (5A2) |

Abbreviations:
G: growth, measuring colony size in diameter
S: colony surface
R: reverse These characteristics were observed after 14 days of incubation at 25° C. The color descriptions were based on the Methuen Handbook of Colour[5].

1) Miura, K. and M. Y. Kudo: An agar-medium for aquatic Hyphomycetes., Trans. Ycolo. Soc. Japan, 11:116–118, 1970.
2) Arx, J. A. von: The Genera of Fungi—Sporulating in Pure Culture (3rd ed.), 315 p., J. Cramer, Vaduz, 1974.
3) Sutton, B. C.: The Coelomycetes—Fungi Imperfecti with Pycnidia, Acervuli and Stromata., 696 p., Commonwealth Mycological Instritute, Kew, 1980.
4) Hawksworth, D. L., B. C. Sutton and G. C. Ainsworth: Dictionary of the Fungi (7th ed.), 445 p., Commonwealth Mycological Institute, Kew., 1983.
5) Kornerup, A. and Wanscher, J. H.: Methuen Handbook of Colour (3rd ed.), 252 p., Methuen, London, 1983.

A culture of Coelomycetes strain F-11899 thus named has been deposited with National Institute of Bioscience and Human-Technology Agency of Industrial Science and Technology (former name: Fermentation Research Institute Agency of Industrial Science and Technology) (1-3, Higashi 1-chome, Tsukuba-shi, IBARAKI 305 JAPAN) on Oct. 26, 1989 under the number of FERM BP-2635.

After that, however, we have further studied the classification of the strain F-11899, and have found that the strain F-11899 resembled *Coleophoma empetri* (Rostrup) Petrak 1929 [2), 3), 4)] belonging to the order Coelomycetes, but differed in some pycnidial characteristics: globose or flattened at the base, immersed, and not papillate.

Considering these characteristics, we classified this strain in more detail and renamed it as "Coleophoma sp. F-11899".

In this connection, we have already taken step to amend the name, "Coelomycetes strain F-11899" to "Coleophoma sp. F-11899" with National Institute of Bioscience and Human-Technology Agency of Industrial Science and Technology (former name: Fermentation Research Institute Agency of Science and Technology, on Sep. 21, 1990.

(ii) Production of the compound [Ia] or a salt thereof.

The compound [Ia] or a salt thereof of this invention is produced when the compound [Ia] or a salt thereof-producing strain belonging to the genus Coleophoma is grown in a nutrient medium containing sources of assimilable carbon and nitrogen under aerobic conditions (e.g. shaking culture, submerged culture, etc.) in the presence of leucine. It is desirable to contain leucine between about 0.05% and 5% (more preferably between about 0.1% and 1%) in a nutrient medium.

The preferred sources of carbon in the nutrient medium are carbohydrates such as glucose, sucrose, starch, fructose or glycerin, or the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid, or the like.

The carbon and nitrogen sources, though advantageously employed in combination, need not to be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salts, or cobalt salts, or the like.

If necessary, especially when the culture medium foams seriously a defoaming agent, such as liquid paraffin, fatty oil, plant oil, mineral oil or silicone, or the like may be added.

As in the case of the preferred methods used for the production of other biologically active substances in massive amounts, submerged aerobic cultural conditions are preferred for the production of the compound [Ia] or a salt thereof in massive amounts.

For the production in small amounts, a shaking or surface culture in a flask or bottle is employed.

Further, when the growth is carried out in large tanks, it is preferable to use the vegetative form of the organism for inoculation in the production tanks in order to avoid growth lag in the process of production of the compound [Ia] or a salt thereof. Accordingly, it is desirable first to produce a vegetative inoculum of the organism by inoculating a relatively small quantity of culture medium with spores or mycelia of the organism and culturing said inoculated medium, and then to transfer the cultured vegetative inoculum to large tanks. The medium, in which the vegetative inoculum is produced, is substantially the same as or different from the medium utilized for the production of the compound [Ia] or a salt thereof.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 20° C. to 30° C., for a period of about 50 hours to 150 hours, which may be varied according to fermentation conditions and scales.

When the fermentation is completed, the culture broth is then subjected for recovery of the compound [Ia] or a salt thereof to various procedures conventionally used for recovery and purification of biological active substances, for instance, solvent extraction with an appropriate solvent or a mixture of some solvents, chromatography or recrystallization from an appropriate solvent or a mixture of some solvents, or the like.

According to this invention, in general, the compound [Ia] or a salt thereof is found both in the cultured mycelia and cultured broth. Accordingly, then the compound [Ia] or a salt thereof is removed from the whole broth by means of extraction using an appropriate organic solvent such as acetone or ethyl acetate, or a mixture of these solvents, or the like.

The extract is treated by a conventional manner to provide the compound [Ia] or a salt thereof, for example, the extract is concentrated by evaporation or distillation to a smaller amount and the resulting residue containing active material, i.e. the compound [Ia] or a salt thereof is purified by conventional purification procedures, for example, chromatography on recrystallization from an appropriate solvent or a mixture of some solvents.

When the object compound is isolated as a salt of the compound [Ia], it can be converted to the free compound [Ia] or another salt of the compound [Ia] according to a conventional manner.

Process 2

The object polypeptide compound [Ib] or a salt thereof can be prepared by subjecting a compound [Ia] or a salt thereof to elimination reaction of N-acyl group.

This reaction is carried out in accordance with a conventional method such as hydrolysis, reduction, reaction with an enzyme or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]-octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.], or the like, is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The reaction with an enzyme can be carried out by reacting the compound [Ia] or a salt thereof with an enzyme suitable for the elimination reaction of N-acyl group.

Suitable example of said enzyme may include the one produced by certain microorganisms of the Streptomyces or the Actinoplanaceae, for example, Streptomyces sp. No. 6907 (FERM BP-5809), *Streptomyces anulatus* No. 4811 (FERM BP-5808), *Streptomyces anulatus* No. 8703 (FERM BP-5810), *Actinoplanes utahensis* IFO-13244, *Actinoplanes utahensis* ATCC 12301, *Actinoplanes missenrienses* NRRL 12053, or the like; and the like.

This elimination reaction is usually carried out in a solvent such as phosphate buffer, Tris-HCl buffer or any other solvent which does not adversely influence the reaction.

The reaction temperature is not critical and the reaction can be carried out at room temperature or under warming.

Process 3

The object polypeptide compound [Ic] or a salt thereof can be prepared by reacting the compound [Ib] or its reactive derivative at the amino group or a salt thereof with the compound [II] or its reactive derivative at the carboxy group or a salt thereof.

Suitable reactive derivative at the carboxy group of the compound [II] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g., methanesulfonic acid, etc.], aliphatic carboxylic acid [e.g., acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-1-(1H)-pyridone, N-hydroxysuccinimide, N-hydroxyphthalimide, 1-hydroxy-1H-benzotriazole, etc.], and the like. These reactive derivatives can optionally be selected from them the mind of the compound [II] to be used.

Suitable salts of the compound [II] and its reactive derivative can be referred to the ones as exemplified for the object polypeptide compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [II] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N-carbonylbis-(2-methylimidazole); pentamethyleneketene-N-cyclohexylimine; diphenylketene-N-cyclohexylimine; ethoxyacetylene; 1-alkoxy-2-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thienyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g., 4-dimethylaminopyridine, etc.), N-(lower)alkylmorpholine, N,N-di(lower)alkylbenzylamine, or the like.

The reaction temperature is not critical, and the reaction is usually carried out under cooling to warming.

The compounds obtained by the above Processes 1 to 3 can be isolated and purified by a conventional method such as pulverization, recrystallization, column-chromatography, high-performance liquid chromatography (HPLC), reprecipitation, or the like.

The compounds obtained by the above Processes 1 to 3 may be obtained as its hydrate, and its hydrate is included within the scope of this invention.

It is to be noted that each of the object polypeptide compound [I] may include one or more stereoisomer such as optical isomer(s) and geometrical isomer(s) due to asymmetric carbon atom(s) and double bond(s) and all such isomers and mixture thereof are included within the scope of this invention.

Biological Property of the Polypeptide Compound [I] of the Present Invention

In order to show the usefulness of the polypeptide compound [I] of the present invention, the biological data of the representative compound is explained in the following.

Test (Antimicrobial activity):

Test Compound The object compound of Example 1

Test Method:

Antimicrobial activity of the object compound of Example 1 was determined by a serial broth dilution method using 96-well microtiter plate in 100 µl of MEM (Eagle's minimum essential medium) for *Candida albicans* and in 100 µl of yeast nitrogen base dextrose medium for both *Asperaillus fumigatus* and *Cryptococcus neoformans*. The inoculum was adjusted to $1\times10^5$ colony forming units/ml. *Candida albicans* and *Asperaillus fumigatus* were cultured at 37° C. for 24 hours and *Cryptococcus neoformans* was cultured at 37° C. for 48 hours in 5% $CO_2$ incubator. After incubation, the growth inhibition of microorganisms in each well was determined by microscopic observation. The results were shown as MEC (minimum effective concentration: µg/ml) value (Table 2).

Test Result

TABLE 2

| Microorganisms | MEC (µg/ml) |
| --- | --- |
| *Candida albicans* FP633 | 0.04 |
| *Aspergillus fumigatus* FP1305 | 0.08 |

From the test result, it is realized that the object polypeptide compound [I] of the present invention has an antimicrobial activity (especially, antifungal activity).

The pharmaceutical composition of the present invention can be used in the form of a pharmaceutical preparation, for example, in solid, semisolid or liquid form, which contains the object polypeptide compound [I] or a pharmaceutically acceptable salt thereof, as an active ingredient in admixture with an organic or inorganic carrier or excipient which is suitable for rectal; pulmonary (nasal or buccal inhalation); ocular; external (topical); oral administration; parenteral (including subcutaneous, intravenous and intramuscular) administrations; insufflation (including aerosols from metered dose inhalator); nebulizer; or dry powder inhalator.

The active ingredient may be compounded, for example, with the usual non-toxic, pharmaceutically acceptable carriers in a solid form such as granules, tablets, dragees, pellets, troches, capsules, or suppositories; creams; ointments; aerosols; powders for insufflation; in a liquid form such as solutions, emulsions, or suspensions for injection; ingestion; eye drops; and any other form suitable for use. And, if necessary, there may be included in the above preparation auxiliary substance such as stabilizing, thickening, wetting, emulsifying and coloring agents; perfumes or buffer; or any other commonly may be used as additives.

The object polypeptide compound [I] or a pharmaceutically acceptable salt thereof is/are included in the pharmaceutical composition in an amount sufficient to produce the desired antimicrobial effect upon the process or condition of diseases.

For applying the composition to human, it is preferable to apply it by intravenous, intramuscular, pulmonary, oral administration, or insufflation. While the dosage of therapeutically effective amount of the object polypeptide compound [I] varies form and also depends upon the age and condition of each individual patient to be treated, in the case of intravenous administration, a daily dose of 0.01–20 mg of the object polypeptide compound [I] per kg weight of human being in the case of intramuscular administration, a daily dose of 0.1–20 mg of the object polypeptide compound [I] per kg weight of human being, in case of oral administration, a daily dose of 0.5–50 mg of the object polypeptide compound [I] per kg weight of human being is generally given for treating or preventing infectious diseases.

Especially in case of the treatment of prevention of *Pneumocystis carinii* infection, the followings are to be noted.

For administration by inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol administration is a preferred method of administration. Insufflation is also a desirable method, especially where infection may have spread to ears and other body cavities.

Alternatively, parenteral administration may be employed using drip intravenous administration.

The following Examples are given for the purpose of illustrating the present invention in more detail.

EXAMPLE 1

(1) Fermentation:

An aqueous seed medium (30 ml) containing sucrose 4%, cotton seed flour 2%, soybean powder 2%, $KH_2PO_4$ 1.6% and $CaCO_3$ 0.2% was poured into a 100 ml Erlenmeyer flask and sterilized at 120° C. for 30 minutes. A loopful of Celeophoma sp. F-11899 was inoculated from a slant culture into the flask. The flask was shaken on a rotary shaker (220 rpm, 5.1 cm-throw) at 25° C. for 7 days and then transferred at the rate of 2% to 160 ml of the same sterile seed medium in each of six 500 ml Erlenmeyer flasks. The flasks were shaken on a rotary shaker (220 rpm, 5.1 cm-throw) at 25° C. for 5 days. The resultant seed culture was inoculated to 20 l of sterile production medium consisting of corn meal 4%, glucose 1%, wheat germ 0.5%, cotton seed flour 1.25%, gluten meal 0.25%, $(NH_4)_2SO_4$ 0.6%, $KH_2PO_4$ 1.6%, $Na_2HPO_4.12H_2O$ 1.6%, $Zn(SO_4)_2.7H_2O$ 0.001%, leucine 0.5%, Adekanol LG-109 (deforming agent, Asahi Denka Co., Ltd.) 0.05% and Silicone KM-70 (deforming agent, Shin-Etsu Chemical Co., Ltd.) 0.05% in a 30 l jar fermentor. Fermentation was carried out at 25° C. for 6 days under aeration of 20 l/min and agitation of 250 rpm.

The production of active compound in the fermentation broth was monitored by HPLC analysis.

(2) Isolation:

The cultured broth (16.5 l) was extracted with 16.5 l of acetone by intermittent mixing. The acetone extract was filtered with an aid of diatomaceous earth and concentrated in vacuo to 18 l. The concentrate was passed through a column (1.5 l) of Diaion HP-20 (Mitsubishi Chemical Co., Ltd.). The column was washed with water and 30% aqueous methanol, and eluted with methanol and 60% aqueous acetonitrile containing 0.2% $NaH_2PO_4.2H_2O$. 13 l of water was added to the eluate (8 l) and applied on a column (2 l) of YMC gel (ODS-AM 120-S50, YMC Co., Ltd.). The column was developed with 40% aqueous acetonitrile containing 0.3% $NaH_2PO_4.2H_2O$. To the active fractions (1.38 l) were added 460 ml of 0.5% $NaH_2PO_4.2H_2O$ solution and rechromatographed on YMC gel (2 l), which was developed with the same solvent. The fractions (900 ml) containing Object Compound (1) were collected and concentrated in vacuo to 690 ml. This solution was subjected to preparative HPLC, YMC-packed column (ODS-AM, SH-343-5AM, S-5, 250×20 mm i.d.) with 40% aqueous acetonitrile containing 0.3% $NaH_2PO_4.2H_2O$ as mobile phase and flow rate 9.9 ml/min. The active fractions (310 ml) were concentrated in vacuo to 250 ml and applied to a column rechromatography on preparative HPLC under the same condition as above. Each of fractions (261 ml) was combined and concentrated to an aqueous solution in vacuo. This solution was passed through a column (30 ml) of Diaion HP-20. The column was washed with water and eluted with 80% aqueous methanol. After concentration to an aqueous solution, the eluate was lyophilized to give 53.2 mg of Object Compound (1) as a white powder.

(HPLC condition); Column: ODS-AM303 (YMC, 250× 4.6 mm i.d.); Eluent: 50% aqueous acetonitrile, 0.25% $NaH_2PO_4.2H_2O$; Flow rate: 1 ml/min. Detection: UV at 210 nm; Retention time: 8.4 min.

The Object Compound (1) as obtained has the following physico-chemical properties.

Appearance: white powder; Nature: acid substance; Melting point: 165–170° C. (dec.); Specific rotation: $[\alpha]_D^{23}$ –23° (C: 0.5, methanol); Molecular formula: $C_{50}H_{79}N_8O_{21}SNa$; Elemental Analysis: Calcd.: for $C_{50}H_{79}N_8O_{21}SNa.6H_2O$ C, 46.51, H, 7.10, N, 8.68, S, 2.48 (%); Found: C, 46.25, H, 7.40, N, 8.86, S, 2.14 (%); Molecular weight: ESI-MS (m/z)=1161 ($M^+$+1); Solubility: soluble: methanol, water; slightly soluble: ethyl acetate, acetone; insoluble: chloroform; Color reaction:

positive: iodine vapor reaction, cerium sulfate reaction; negative: Dragendorff reaction, Molish reaction; Thin layer chromatography (TLC):

| Stationary phase | Developing solvent | Rf value |
| --- | --- | --- |
| silica gel* | n-butanol:acetic acid:water (4:1:2) | 0.33 |

*Silica Gel 60 $F_{254}$ plate (made by E. Merck)

Ultraviolet Absorption Spectrum: $\lambda_{max}^{methanol}$ ($E_{1\ cm}^{1\%}$): 201 (564), 221 (246), 274 (16.0)$_{nm}$; $\lambda_{max}^{methanol+0.01}$N-NaOH ($E_{1\ cm}^{1\%}$): 204.5 (1081), 246 (52), 284 (15.5)$_{nm}$; Infrared absorption spectrum: $\lambda_{max}^{KBr}$: 3360, 2920, 2850, 1650, 1640, 1520, 1440, 1270, 1050 $cm^{-1}$; $^1$H-NMR ($CD_3OD$, 500 MHz); δ: 0.89 (3H, t, J=7 Hz), 1.16 (3H, d, J=7 Hz), 1.23–1.34 (24H, m), 1.57 (2H, m), 1.92–2.02 (4H, m), 2.20 (2H, m), 2.26 (1H, m), 2.38 (1H, m), 2.47 (1H, dd, J=16 and 9.5 Hz), 2.74 (1H, dd, J=16 and 4 Hz), 3.72–3.81 (2H, m), 3.90–4.00 (3H, m), 4.25–4.29 (2H, m), 4.33–4.39 (2H, m), 4.46 (1H, dd, J=11 and 6.5 Hz), 4.51–4.58 (3H, m), 4.93 (1H, d, J=3 Hz), 5.08 (1H, d, J=4 Hz), 5.25 (1H, d, J=3 Hz), 6.84 (1H, d, J=8 Hz), 7.01 (1H, dd, J=8 and 2 Hz), 7.30 (1H, d, J=2 Hz); $^{13}$C-NMR ($CD_3OD$, 125 MHz); δ: 14.4 (q), 19.8 (q), 23.7 (t), 27.0 (t), 30.3 (t), 30.4 (t), 30.5 (t), 30.6 (t), 30.7 (t), 30.8 (t×5), 33.1 (t), 34.6 (t), 34.9 (t), 36.7 (t), 38.4 (t), 39.6 (t), 47.0 (t), 51.4 (d), 55.5 (d), 56.9 (d), 57.1 (t), 58.4 (d), 62.4 (d), 68.2 (d), 69.7 (d), 70.7 (d), 70.7 (d), 71.4 (d), 74.1 (d), 74.3 (d), 75.5 (d), 76.3 (d), 118.2 (d), 123.2 (d), 125.6 (d), 134.5 (s), 141.1 (s), 150.3 (s), 169.3 (s), 172.6 (s), 172.7 (s), 172.8 (s), 173.6 (s), 174.4 (s), 175.8 (s), 176.9 (s).

From the analysis of the above physical and chemical properties, and the result of the further investigation of identification of chemical structure, the chemical structure of the Object Compound (1) has been identified and assigned as follows.

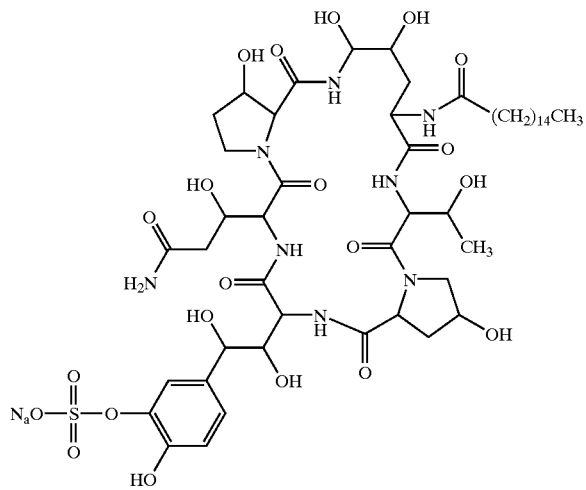

EXAMPLE 2

(1) Fermentation of *Actinoplanes utahensis*

A stock culture of *Actinoplanes utahensis* IFO-13244 is prepared and maintained on agar slant. A loopful of the slant culture was inoculated into a seed medium consisted of starch 1%, sucrose 1%, glucose 1%, cotton seed flour 1%, peptone 0.5%, soy bean meal 0.5% and $CaCO_3$ 0.1%. The inoculated vegetative medium was incubated in a 225 ml wide mouth Erlenmeyer flask at 30° C. for about 72 hours on a rotary shaker.

This incubated vegetative medium was used directly to inoculate into a production medium (20 l) consisted of sucrose 2%, peanut powder 1%, $K_2HPO_4$ 0.12%, $KH_2PO_4$ 0.05% and $MgSO_4.7H_2O$ 0.025%. The inoculated production medium was allowed to ferment in a 30 l jar fermentor at a temperature of 30° C. for about 80 hours. The fermentation medium was stirred with conventional agitators at 250 rpm and aerated at 20 l per minute. The vegetative mycelium was collected from the fermented broth by filtration and once washed with water. The washed mycelium was directly used to obtain the Object Compound (2).

(2) Reaction Condition

To a solution of the Object Compound (1) (10 g) in water (1000 ml) was added 250 ml of 1M Na-phosphate buffer (pH 5.8) and 1000 ml of water and a 250 g wet weight of washed mycelium of *Actionoplanes utahensis* IFO-13244 which was obtained by above fermentation. The reaction was carried out at 50° C. with stirring for 3 hours. Increase of the Object Compound (2) was monitored by analytical HPLC indicated below.

From a 10 g of the Object Compound (1), a 6.8 g of the Object Compound (2) was formed in the reaction mixture.

(HPLC condition); Column: YMC Pack ODS-AM AM303, S-5 120A (250 mm L.×4.6 mm I.D., YMC Co., Ltd.); Eluent: 3% aqueous acetonitrile, 0.5% $NaH_2PO_4.2H_2O$; Flow rate: 1 ml/min. Detection: UV at 210 nm Retention time: 6.1 min.

The Object Compound (2) as obtained has the following physico-chemical properties.

Appearance: white powder; Melting point: 150–155° C.; Specific rotation: $[\alpha]_D^{23}$ –26° (C: 0.5, $H_2O$); Molecular formula: $C_{34}H_{50}N_8O_{20}S$; Molecular weight: ESI-MS (m/z)= 923 ($M^+$+1); Solubility: soluble: water; slightly soluble: methanol; insoluble: ethyl acetate, n-hexane; Color reaction: positive: iodine vapor reaction, cerium sulfate reaction, ninhydrin; negative: $FeCl_3$, Molish reaction; Thin layer chromatography (TLC):

| Stationary phase | Developing solvent | Rf value |
|---|---|---|
| silica gel* | 70% 2-propanol aqueous solution | 0.55 |

*Silica Gel 60 $F_{254}$ plate (made by E. Merck)

Infrared absorption spectrum: $\lambda_{max}^{KBr}$: 3400, 2940, 1670, 1630, 1540, 1520, 1440, 1280, 1250, 1080, 1050, 950 $cm^{-1}$; $^1$H-NMR ($D_2O$, 500 MHz) δ: 1.23 (3H, d, J=6.5 Hz), 1.97–2.13 (3H, m), 2.29–2.53 (5H, m), 3.76–3.80 (2H, m), 3.90 (1H, br d, J=12 Hz), 4.02–4.10 (2H, m), 4.16–4.21 (3H, m), 4.37–4.42 (2H, m), 4.45–4.48 (2H, m), 4.55 (1H, m), 4.60 (1H, m), 4.71 (1H, m), 4.92 (1H, d, J=6 Hz), 5.01 (1H, d, J=3.5 Hz), 5.38 (1H, d, J=3 Hz), 7.03 (1H, d, J=8 Hz), 7.09 (1H, dd, J=2 and 8 Hz), 7.27 (1H, d, J=2 Hz); $^{13}$C-NMR ($D_2O$, 125 MHz) δ: 55.3 (d), 57.0 (d), 58.1 (d), 58.4 (t), 60.2 (d), 63.9 (d), 69.4 (d), 70.2 (d), 71.5 (d), 72.8 (d), 73.0 (d), 75.2 (d), 77.1 (d), 77.2 (d), 78.1 (d), 120.5 (d), 124.7 (d), 128.3 (d), 134.5 (s), 141.6 (s), 151.1 (s), 171.1 (s), 172.2 (s), 174.1 (s), 174.4 (s), 174.5 (s), 176.2 (s), 178.4 (s).

From the analysis of the above physical and chemical properties, and the result of the further investigation of identification of chemical structure, the chemical structure of the Object Compound (2) has been identified and assigned as follows.

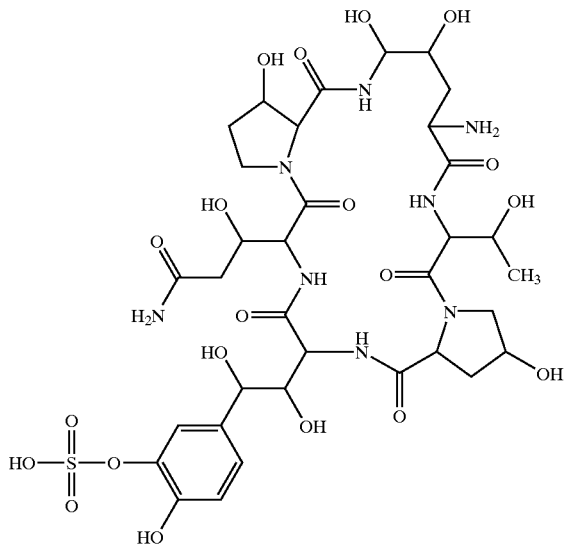

The Starting Compound in the following Examples 3 to 8 and The Object Compounds (3) to (8) in the following Examples 3 to 8 are illustrated by chemical formulae as below.

The Starting Compound (the same in Examples 3 to 8)

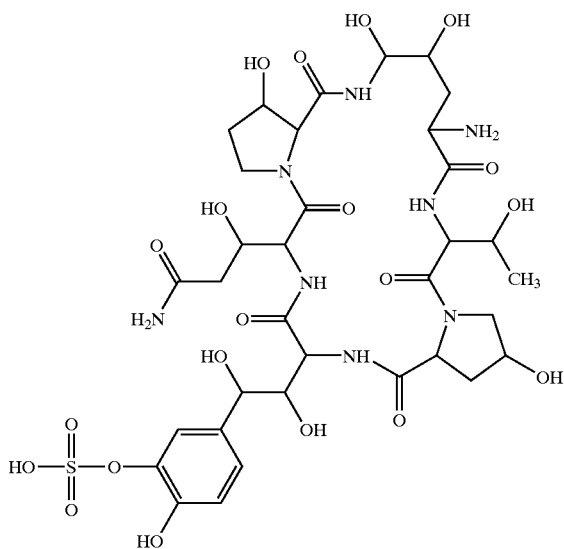

The Object Compounds (3) to (8)

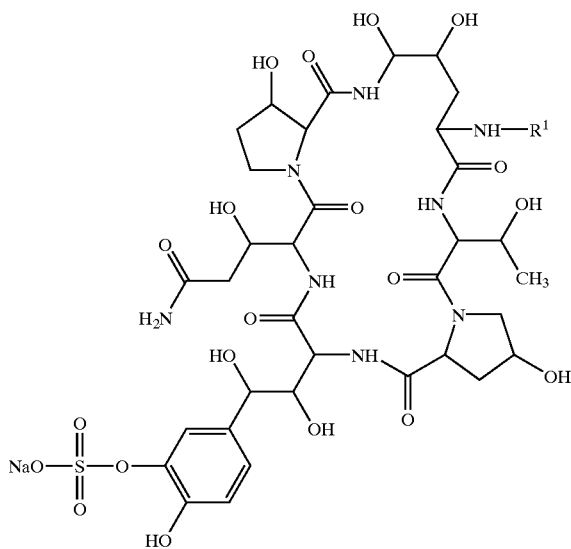

In the following Examples, The Object Compound (X) [e.g. The Object Compound (3)] means the object compound of Example (X) [e.g. Example (3)].

| Example No. | R¹ |
|---|---|
| 3 | —CO—⌬—N(piperazine)N—⌬—O—(CH$_2$)$_5$CH$_3$ |
| 4 | —CO—⌬—(1,3,4-thiadiazole)—⌬—O—(CH$_2$)$_5$CH$_3$ |

-continued

| Example No. | R¹ |
|---|---|
| 5 | —CO—⌬—(isoxazole N—O)—⌬—O—(CH$_2$)$_4$CH$_3$ |
| 6 | —CO—CH=CH—⌬—⌬—O—(CH$_2$)$_4$CH$_3$ |
| 7 | —CO—⌬—O—(CH$_2$)$_7$CH$_3$ |
| 8 | —CO—⌬—⌬—⌬—O—(CH$_2$)$_4$CH$_3$ |

EXAMPLE 3

To a solution of Starting Compound (150 mg) and 4-[4-(4-hexyloxyphenyl)piperazin-1-yl]benzoic acid benzotriazol-1-yl ester (81 mg) in N,N-dimethylformamide (3.5 ml) was added diisopropylethylamine (0.032 ml), and stirred for 4 hours at ambient temperature. The reaction mixture was pulverized with ethyl acetate. The precipitate was collected by filtration, and dried under reduced pressure. The powder was dissolved in water, and subjected to column chromatography on ion exchange resin (DOWEX-50WX4 (Trademark: prepared by Dow Chemical)) eluting with water. The fractions containing the object compound were combined, and subjected to column chromatography on ODS (YMC-gel.ODS-AM.S-50 (Trademark: prepared by Yamamura Chemical Lab.)) eluting with 20% acetonitrile aqueous solution. The fractions containing the object compound were combined, and evaporated under reduced pressure to remove acetonitrile. The residue was lyophilized to give Object Compound (3).

IR (KBr): 3359, 1668, 1629, 1537, 1510 cm$^{-1}$; NMR (DMSO-d$_6$, δ): 0.88 (3H, t, J=6.7 Hz), 1.05 (3H, d, J=5.7 Hz), 1.29–1.5 (6H, m), 1.5–1.71 (2H, m), 1.71–2.04 (3H, m), 2.04–2.4 (4H, m), 2.59 (1H, m), 3.16 (4H, m), 3.4–3.7 (1H, m), 3.72 (2H, m), 3.8–4.0 (6H, m), 4.0–4.29 (6H, m), 4.29–4.5 (5H, m), 4.74 (2H, d, J=5.7 Hz), 4.8–5.1 (6H, m), 5.16 (1H, d, J=3.2 Hz), 5.22 (2H, d, J=3.5 Hz), 5.47 (2H, d, J=6.2 Hz), 6.73 (1H, d, J=8.5 Hz), 6.83 (2H, d, J=8.5 Hz), 6.92 (1H, s), 6.98 (2H, d, J=3.6 Hz), 7.03 (2H, s), 7.30–7.45 (3H, m), 7.82 (2H, d, J=8.5 Hz), 8.07 (1H, d, J=7.2 Hz), 8.27 (1H, d, J=7.2 Hz), 8.43 (1H, d, J=7.2 Hz), 8.84 (1H, s); MASS (m/z): 1330.73 (M+Na$^+$); Elemental Analysis Calcd. for $C_{57}H_{77}N_{10}O_{22}SNa.22H_2O$: C, 40.14, H, 7.15, N, 8.21; Found: C, 40.00, H, 5.73, N, 8.20.

The following Object Compounds (4) to (8) were obtained according to a similar manner to that of Example 3.

EXAMPLE 4

IR (KBr): 3359, 1668, 1650, 1631 cm$^{-1}$; NMR (DMSO-d$_6$, δ): 0.89 (3H, t, J=6.7 Hz), 1.17 (3H, d, J=6.0 Hz), 1.3–1.47 (6H, m), 1.5–2.0 (6H, m), 2.0–2.4 (5H, m), 3.5–4.2 (12H, m), 4.3–4.5 (4H, m), 4.5–4.75 (4H, m), 4.84 (1H, s), 4.9–5.4 (6H, m), 6.64 (2H, d, J=8.0 Hz), 6.83 (2H, m), 6.9–7.2 (6H, m), 7.8–8.15 (6H, m), 8.31 (1H, m), 8.78 (1H, m) MASS (m/z): 1285.40 (M-Na$^+$); Elemental Analysis Calcd. for $C_{49}H_{69}N_8OO_{22}SNa.11H_2O$: C, 45.45, H, 5.89, N, 9.64; Found: C, 45.31, H, 5.88, N, 9.54.

EXAMPLE 5

IR (KBr): 3363, 1648, 1619, 1506, 1257 cm$^{-1}$; NMR (DMSO-d$_6$, δ): 0.91 (3H, t, J=7.1 Hz), 1.09 (3H, d, J=5.9 Hz), 1.29–1.5 (4H, m), 1.6–2.4 (9H, m), 2.58 (1H, m), 3.5–4.6 (16H, m), 4.8–5.3 (11H, m), 5.53 (1H, d, J=5.9 Hz), 6.73 (1H, d, J=8.3 Hz), 6.83 (1H, d, J=8.3 Hz), 6.85 (1H, s), 7.05 (1H, s), 7.12 (2H, d, J=8.9 Hz), 7.25 (1H, s), 7.3–7.4 (2H, m), 7.55 (1H, s), 7.85 (2H, d, J=8.9 Hz), 7.9–8.1 (5H, m), 8.29 (1H, d, J=5 Hz), 8.85 (1H, s), 8.87 (1H, d, J=8.7 Hz); MASS (m/z): 1254 (M–Na$^+$); Elemental Analysis Calcd. for $C_{55}H_{68}N_9O_{23}SNa.8H_2O$: C, 46.44, H, 5.95, N, 8.86; Found: C, 46.30, H, 5.78, N, 8.76.

EXAMPLE 6

IR (KBr): 3359, 1655, 1631, 1537, 1519 cm$^{-1}$; NMR (DMSO-d$_6$, δ): 0.91 (3H, t, J=6.7 Hz), 1.09 (3H, d, J=5.7 Hz), 1.29–1.5 (4H, m), 1.5–2.0 (6H, m), 2.0–2.4 (3H, m), 2.59 (1H, m), 3.5–3.9 (4H, m), 3.9–4.5 (13H, m), 4.78 (2H, d, J=5.7 Hz), 4.8–4.95 (2H, d, J=5.7 Hz), 5.02 (3H, s), 5.1–5.25 (3H, m), 5.51 (1H, d, J=6.0 Hz), 6.73 (2H, d, J=8.0 Hz), 6.7–6.8 (2H, d, J=9.0 Hz), 7.02 (3H, d, J=9.0 Hz), 7.3–7.5 (4H, m), 7.65 (6H, m), 8.09 (1H, d, J=7.2 Hz), 8.29 (1H, d, J=7.2 Hz), 8.50 (1H, d, J=7.2 Hz), 8.84 (1H, s); MASS (m/z): 1213.73 (M–Na$^+$); Elemental Analysis Calcd. for $C_{54}H_{69}N_8O_{22}SNa.17H_2O$: C, 42.02, H, 6.73, N, 7.26; Found: C, 41.87, H, 5.91, N, 7.28.

EXAMPLE 7

IR (KBr): 3359, 1668, 1632, 1539 cm$^{-1}$; NMR (DMSO-d$_6$, δ): 0.86 (3H, t, J=6.7 Hz), 1.05 (3H, d, J=6.7 Hz), 1.27 (10H, m), 1.72 (2H, t, J=6.7 Hz), 1.75–2.3 (7H, m), 2.58 (1H, m), 3.61 (1H, m), 3.72 (2H, s), 3.8–4.5 (17H, m), 4.73 (2H, d, J=6.0 Hz), 4.8–5.1 (5H, m), 5.1–5.3 (3H, m), 5.47 (1H, d, J=6.0 Hz), 6.73 (1H, d, J=8.3 Hz), 6.81 (1H, s), 7.15 (2H, d, J=8.3 Hz), 7.30 (1H, s), 7.2–7.5 (3H, m), 7.73 (2H, d, J=6.4 Hz), 7.86 (1H, d, J=8.7 Hz), 8.05 (1H, d, J=8.7 Hz), 8.27 (1H, d, J=8.7 Hz), 8.54 (1H, d, J=8.7 Hz), 8.84 (1H, s); MASS (m/z): 1153.69 (M–Na$^+$); Elemental Analysis Calcd. for $C_{49}H_{69}N_8O_{22}SNa.11H_2O$: C, 42.79, H, 6.67, N, 8.15; Found: C, 42.97, H, 6.64, N, 8.10.

EXAMPLE 8

IR (KBr): 3359, 1668, 1648, 1632, 1537 cm$^{-1}$; NMR (DMSO-d$_6$, δ): 0.91 (3H, t, J=6.7 Hz), 1.09 (3H, d, J=6.7 Hz), 1.75 (4H, m), 1.5–2.4 (9H, m), 2.59 (1H, m), 3.60 (1H, m), 3.73 (2H, s), 3.8–4.1 (5H, m), 4.1–4.3 (5H, m), 4.3–4.6 (4H, m), 4.78 (2H, d, J=5.8 Hz), 4.8–5.1 (5H, m), 5.17 (1H, d, J=2.9 Hz), 5.23 (2H, t, J=4.9 Hz), 5.52 (1H, d, J=7.5 Hz), 6.74 (1H, d, J=8.2 Hz), 6.83 (2H, d, J=7.3 Hz), 7.04 (3H, d, J=8.2 Hz), 7.29–7.45 (3H, m), 7.67 (2H, d, J=8.8 Hz), 7.72 (1H, s), 7.80 (4H, t, J=8.1 Hz), 8.01 (2H, d, J=8.1 Hz), 8.08 (1H, d, J=8.6 Hz), 8.30 (1H, d, J=7.8 Hz), 8.78 (1H, d, J=7.8 Hz), 8.85 (1H, s); MASS (m/z): 1262.98 (M–Na$^+$); Elemental Analysis Calcd. for $C_{58}H_{71}N_8O_{22}SNa.8H_2O$: C, 48.67, H, 6.13, N, 7.83; Found: C, 48.72, H, 6.07, N, 7.72.

---

What is claimed is:

1. A polypeptide compound of the following general formula [I]:SEQ ID NO: 1:

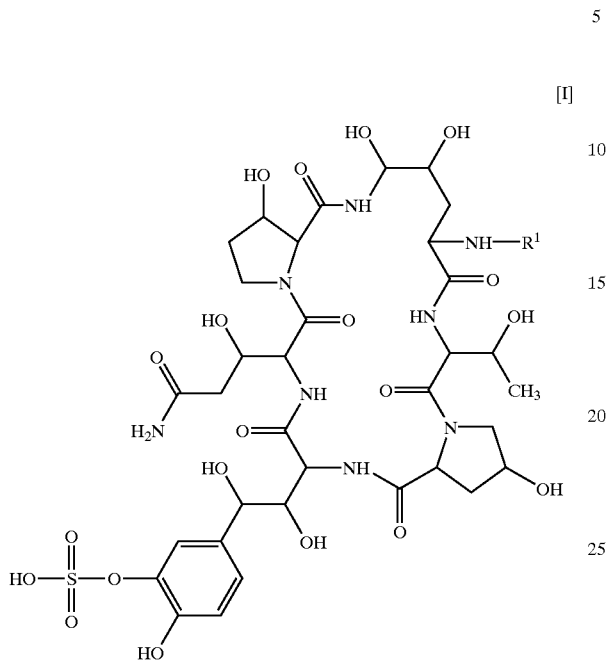

wherein R¹ is hydrogen or acyl group, or a salt thereof.

2. A compound of claim 1, wherein

R¹ is hydrogen, lower alkanoyl, higher alkanoyl, lower alkenoyl, higher alkenoyl, lower alkoxycarbonyl, higher alkoxycarbonyl, aryloxycarbonyl, arylglyoxyloyl, ar(lower)alkoxycarbonyl, lower alkylsulfonyl, arylsulfonyl, ar(lower)alkylsulfonyl, aroyl substituted with higer alkoxy, aroyl substituted with heterocyclic group which has aryl having lower alkoxy, aroyl substituted with heterocyclic group which has aryl having higher alkoxy, ar(lower)alkenoyl substituted with aryl having lower alkoxy, ar(lower) alkenoyl substituted with aryl having higher alkoxy, aroyl substituted with aryl which has aryl having lower alkoxy or aroyl substituted with aryl which has aryl having higher alkoxy.

3. A compound of claim 2, wherein

R¹ is hydrogen, higher alkanoyl, aroyl substituted with higher alkoxy, aroyl substituted with heterocyclic group which has aryl having lower alkoxy, aroyl substituted with heterocyclic group which has aryl having higher alkoxy, ar(lower)alkenoyl substituted with aryl having lower alkoxy or aroyl substituted with aryl which has aryl having lower alkoxy.

4. A process for preparing a polypeptide compound of the following general formula [I] (SEQ ID NO: 1):

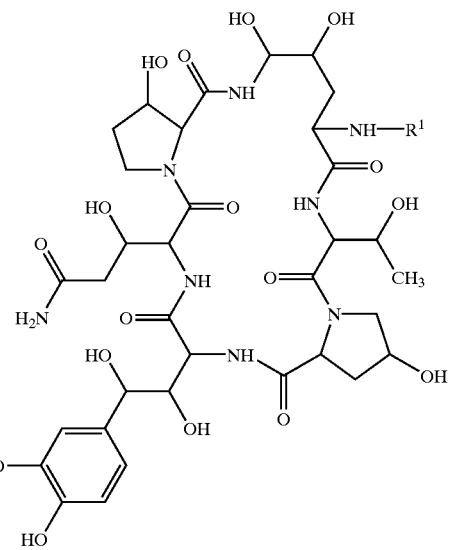

wherein R¹ is hydrogen or acyl group, or a salt thereof, which comprises i) fermenting the strain F-11899 belonging to the genus Coleophoma which is capable of producing a compound of the formula [Ia] or a salt thereof:

[Ia]

in a nutrient medium in the presence of leucine and recovering the compound [Ia] or a salt thereof, to give the compound [Ia] or a salt thereof, or ii) subjecting a compound of [Ia] or a salt thereof, to elimination reaction of N-acyl group, to give a compound of the formula [Ib]:

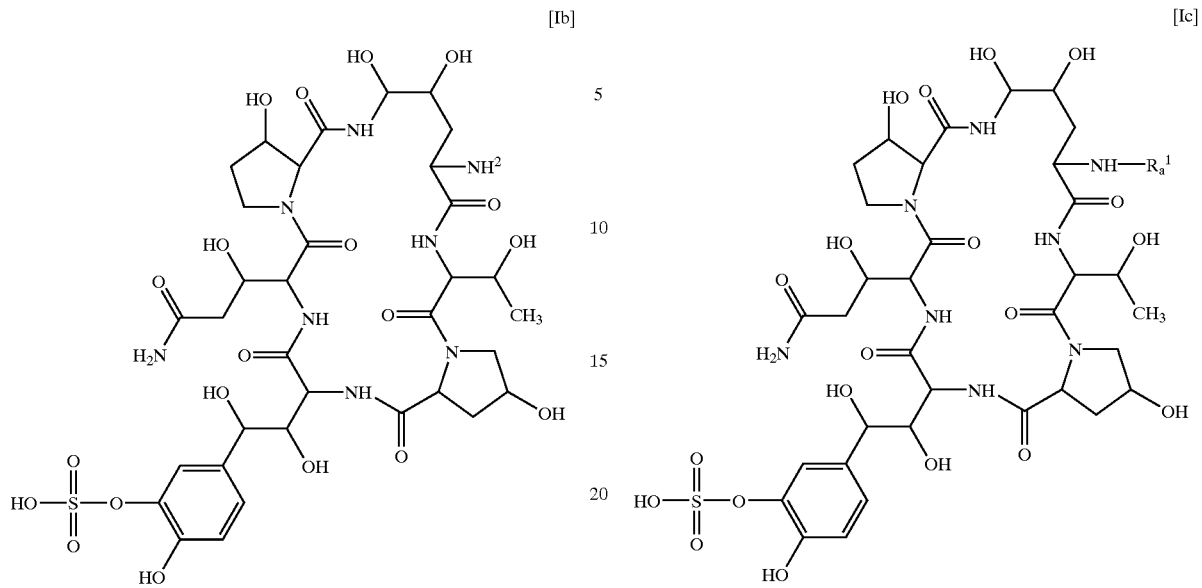

or a salt thereof, or iii) reacting a compound of [Ib] or a salt thereof, with a compound [II] of the formula $$R_a^1\text{—OH} \quad [II]$$

or its reactive derivative at the carboxy group or a salt thereof, to give a compound of the formula [Ic]:

wherein $R_a^1$ is acyl, group, or a salt thereof.

5. A pharmaceutical composition which comprises, as an active ingredient, a compound of claim 1 or a pharmaceutically acceptable salt thereof in admixture with a pharmaceutically acceptable carrier or excipient.

6. A process for the prophylactic and/or the therapeutic treatment of infectious diseases caused by pathogenic microorganisms which comprises administering a compound of claim 1 or a pharmaceutically acceptable salt thereof to a human being or an animal.

7. A polypeptide compound according to claim 1 wherein $R^1$ is hydrogen.

* * * * *